United States Patent [19]

Morimoto et al.

[11] Patent Number: 5,075,230

[45] Date of Patent: Dec. 24, 1991

[54] STABILIZED PLASMINOGEN ACTIVATOR PRECURSOR AND METHOD OF PRODUCING THE SAME

[75] Inventors: Kazuo Morimoto, Fukuchiyama; Motoshi Sagane, Joyo; Kazuhiro Ohara; Shusaku Narita, both of Fukuchiyama, all of Japan

[73] Assignee: The Green Cross Corporation, Osaka, Japan

[21] Appl. No.: 512,511

[22] Filed: Apr. 20, 1990

Related U.S. Application Data

[63] Continuation of Ser. No. 823,755, Jan. 29, 1988, abandoned.

[30] Foreign Application Priority Data

Jan. 30, 1985 [JP] Japan ................... 60-17077

[51] Int. Cl.$^5$ .................. C12N 9/96; C12N 9/72
[52] U.S. Cl. .................. 435/188; 435/212; 435/215
[58] Field of Search .................. 435/188, 212, 215

[56] References Cited

U.S. PATENT DOCUMENTS

| | | | |
|---|---|---|---|
| 3,950,223 | 4/1976 | Yugari et al. | 195/68 |
| 4,245,051 | 1/1981 | Reich et al. | 435/212 |
| 4,495,285 | 1/1985 | Shimizu et al. | 435/215 |
| 4,552,760 | 11/1985 | Murakami et al. | 435/215 X |

FOREIGN PATENT DOCUMENTS

| | | |
|---|---|---|
| 0013447 | 7/1980 | European Pat. Off. . |
| 139447 | 5/1985 | European Pat. Off. . |
| 151996 | 8/1985 | European Pat. Off. . |
| 200966 | 11/1986 | European Pat. Off. . |
| 58-170354 | 9/1983 | Japan . |

OTHER PUBLICATIONS

Nonionic Surfactants, vol. 2, 1967, Chapter 3, pp. 44, 45, 74, 75; chapter 18, pp. 604–609.

Monsan, P. et al. (1984), Ann. N.Y. Acad. Sci. 434, 48–60.

Wun, T-C., et al. (1982), J. Biol. Chem. 257(12) 7262–7268.

Nielsen et al., Biochemistry 1982, vol. 21, pp. 6410–6415.

Primary Examiner—Elizabeth C. Weimar
Assistant Examiner—Charles L. Patterson
Attorney, Agent, or Firm—Cushman, Darby & Cushman

[57] ABSTRACT

A plasminogen activator precursor obtainable from a serum-free culture fluid of human kidney cells is stabilized by adding to its solution poly-C1–C5-alkylene glycols, polyethylene-polyoxypropylene copolymers, mandelic acid salts, triethanolamine, acid addition salts of acetylglycillysine methyl ester, guanidine salts, thiocyanic acid salts, alkali metal iodides or serine.

10 Claims, No Drawings

STABILIZED PLASMINOGEN ACTIVATOR PRECURSOR AND METHOD OF PRODUCING THE SAME

This is a continuation of application Ser. No. 06/823,755, filed Jan. 29, 1986, which was abandoned.

This invention relates to a method of stabilizing a plasminogen activator precursor (hereinafter referred to simply as precursor).

The precursor is one of the fibrinolysis-inducing enzymes existing in living bodies. A detail explanation of it is given, for example, in the specification of Japanese Patent Application No. 170354/83 or its corresponding European Patent Application Publication No. 0139447 published on May 2, 1985. The precursor is a so-called zymogen which, though inactive as it is, manifests an enzymatic activity when treated with plasmin. The precursor can be produced, for example, according to a method disclosed in the Japanese Patent Application, which comprises culturing the precursor-producing cells derived from human kidney in a serum-free tissue culturing medium to produce the precursor, subjecting the supernatant of the culture fluid to purification with respect to protein therein, and subjecting the resulting protein solution containing the precursor to affinity chromatography using a column of immobilized anti-precursor antibody.

More specifically, human kidney cells were cultured for 3 days in a serum-free medium to whch 0.1% human serum albumin had been added. The resulting culture fluid was centrifuged and the supernatant was frozen and stored.

The recovery of the enzyme from the culture fluid can be conducted, for example, by treating the fluid with a suitable combination of such means as centrifugation, vacuum concentration, salting-out fractionation, gel filtration, concentration, ion exchange chromatography, and affinity chromatography.

More particularly, the recovery may be conducted, for example, in the following way. The collected culture fluid supernatant is partly purified by ion exchange chromatography. The most suitable carrier for the chromatography is a weakly acidic cation exchanger, which includes, for example, CM-Exchange, or Duo-lite. After conditioning the carrier to pH 4.5 to 6.5, preferably pH 5 to 6, by a buffer solution, the collected solution mentioned above is applied and allowed to be adsorbed onto the carrier. The carrier is washed with the same buffer solution was used in the above pH conditioning and then treated with a buffer solution of pH 7.5 to 9.5, more preferably pH 8 to 9, to elute the present enzyme. Examples of this suitable buffer solution include a phosphate buffer. The eluted material is then highly purified by affinity chromatography. The affinity medium to be used may be either a plyclonal antibody column or a monoclonal antibody column.

The preparation of the above-mentioned antiserum may be carried out by a known method. For example, a mixed emulsion prepared from the highly purified enzyme and Freund's complete adjuvant is injected intracutaneously 2 to 3 times to an animal; blood is collected several days after the final immunization; the collected blood is coagulated at room temperature, allowed to stand overnight at 4° C., and then centrifuged at 3,000 rpm for 20 minutes to give said antiserum.

The animals to be used for immunization are not restricted as to species and include, for example, rates, mice, rabbits, goats and horses. The purification of said antiserum can be conducted, for example, according to the method described in J. Am. Chem. Soc., 62, 3386 (1940) or Fed. Proc., 17, 1161 (1958).

For immobilizing the anti-enzyme antibody without losing its activity, the following insoluble matrices can be used: copolymers of amino acids [J. Biol. Chem. 236, 1970 (1961)], cellulose [Nature, 189, 576 (1961)], agarose or Sephadex [Nature, 215, 1491 (1967)]; Nature, 245, 3059 (1970) ] and polyacrylamide [Biochem., 8, 4704 (1966)]. These means permit effective immobilization of the anti-enzyme antibody. By using the adsorbents thus obtained, the enzyme can be obtained in good yield and high purity.

The affinity chromatography of the enzyme according to this invention can be conducted as follows. The enzyme which has been partly purified by means of a cation exchanger is brought into contact with and adsorbed onto an anti-enzyme antibody column which has been equilibrated with a buffer solution of pH 6 to 8. After being washed, the column is eluted with an aqueous solution of pH 2 to 4.

In the method using polyclonal antibody, the anti-fibrinolysis-related enzyme antibody can be obtained by immunizing an animal with the highly purified enzyme, and recovering and purifying the intended antibody from the resulting serum.

In the method using monoclonal antibody, the anti-enzyme antibody is obtained by cell fusion. The cell fusion an be conducted by a method known per se. For example, a proliferative cell and a lymphocyte which is producing the intended antibody are made to react in the presence of polyethylene glycol, resulting information of a cell which has both proliferative ability and antibody-producing ability. The antibody produced by the cell is a single antibody which reacts only with a single antigenic determinent.

Following is a detailed example of purification of enzyme with the method using monoclonal antibodies. The pooled culture supernatant fluid was adjusted to pH 5.5 and then brought into contact with CM-Sephadex C-50. The column was washed with 0.16M phosphate buffer solution, pH 5.5, and the enzyme which had been adsorbed on the column was then eluted with 0.16M phosphate buffer solution, pH 8.5.

In the meantime, spenic cells of mouse BALB/c, which had been immunized beforehand with the enzyme, and mouse myeloma cells were fused together in the presence of polyethylen glycol. From the resulting hybridoma, those clones which showed a high producing capacity of antibody for the enzyme were selected. From the culture fluid of the fused cell was recovered the anti-enzyme monoclonal antibody. The monoclonal antibody was immobilized on CNBr-activated Sepharose 4B (Pharmacia, Inc.).

The monoclonal antibody column thus prepared was equilibrated with 0.1m phosphate buffer solution, pH 7.0, containing 0.4M NaCl, and the above-mentioned eluate containing the enzyme was brought into contact with the column. The column was washed with 0.1M phosphate buffer solution, pH 7.0, containing 0.4M NaCl, and then the enzyme which had been adsorbed on the column was eluted with 0.2M aqueous glycine-HCl solution, pH 2.5, containing 0.15M NaCl. The elute was aseptically filtered and then lyophilized to give a highly purified enzyme.

The recovery was about 90%. In SDS-polyacrylamide gel electrophoresis, the purified product showed a single band corresponding to a molecular weight of 50,000 daltons.

The method of recover described above gives merely an example of the method of recovering the enzyme of this invention, and it is needless to say that other methods may also be used for the recovery.

The precursor thus obtained has a single-chained structure consisting of 411 amino acids, has a molecular weight of 53,000 and has an utterly different property from that of previous urokinase (hereinafter referred to as UK) in that it has a specific affinity for fibrin and undergoes no immunoreaction with antiurokinase antibody.

Though the precursor shows no enzymatic activity, it is precursor of urokinase, since plasminogen activator activity which is manifested by plasmin treatment of the precursor is completely inhibited by antiurokinase antibody. The precursor has a different thrombolytic characteristic from that of previous urokinase (hereinafter abbreviate as UK) in that it has a specific affinity for fibrin and selectively decomposes fibris which is a fiber constituting a thrombus. This precursor, which has an excellent characteristic different from that of UK, is expected to be widely used clinically as a fibrinolysis-inducing enzyme by virtue of its property different from that of UK. Though its activity cannot be determined by the synthetic substrate method, it can be determined by the plating method.

In general, proteins tend to be unstable in solutions. The precursor has also possibly a similar tendency. Accordingly, it is understood that the precursor undergoes denaturation, decomposition, or decrease in titer during the purification step or the rapid freeze-thawing step.

The above-mentioned European Patent Application Publication discloses albumin for stabilizing the precursor. However, albumin sometimes forms a polymer, and there is a fear of the problem of antigenicity when it is contained in final medical preparations.

Accordingly, the object of this invention is to provide a method of stabilizing the precursor which method is free from the problem of antigenicity, and the stabilized precursor.

The present inventors have made extensive studies to solve these problems. As a result, it has been found that gelatin, polyalkylene glycols, polyoxyethylene-polyoxypropylene copolymers, mandelic acid salts, triethanolamine, acid addition salts of acetylglycillysime methyl ester, guanidine salts, thiocyanic acid salts, alkali metal iodides, and serine have a stabilizing effect for the precursor. This invention has been accomplished on the basis of the finding.

Thus, this invention relates to a method of stabilizing a plasminogen activator precursor comprising adding to a solution of the precursor at least one stabilizer selected from gelatin, polyalkylene glycols, polyoxyethylene-polyoxypropylene copolymers, mandelic acid salts, triethanolamine, acid addition salts of acetylglycillysine methyl ester, guanidine salts, thiocyanic acid salts. alkali metal iodides, and serine.

The precursor used in this invention is not specifically limited as to its origin, and include, for example, one derived from plasma, one obtained by cultivating human kidney cells in serum-free medium, and one obtained by a process based on genetic engineering. In this connection, the method of cultivating kidney cells and the process for recovery and purification of the precursor are disclosed in aforementioned Japanese Patent Application No. 170354/83 (European Patent Application Publication No. 0139447).

Though the purity of the precursor is not specifically restricted in this invention, the stabilizing effect according to this invention generally tends to be large when the concentration (activity) of the precursor is low. For example, a concentration approximately in the range of 100 to 2,000 IU/ml is used. ("IU" is the abbreviation of "international unit of UK"). One IU/Ml means that when 1 ml of a precursor solution is treated with plasmin, the resulting solution has an activity equivalent to 1 IU of UK. The same applies hereinafter.

The alkylene groups in the polyalkylene glycols used in this invention are preferably those having 1 to 5 carbon atoms, such as methylene and ethylene. Said polyalkylene glycols have preferably a molecular weight of 3,000 to 10,000.

The polyoxyethylene-polyoxyproylene copolymers have preferably a molecular weight of 2,000 to 20,000. Specific examples thereof include Pluronic (a registered trade name F68.

Examples of mandelic acid salts to be used include alkali metal salts, such as sodium or potassium salt, and alkaline earth metal salts such as magnesium or calcium salt.

Examples of the acid addition salts of acetylglycilly-sine methyl ester (Ac-Gly-Lys-OMe) are physiologically acceptable ones and include organic acid salts such as acetate and inorganic acid salts such as hydrochloride and sulfuric acid salt.

Preferred examples of the guanidine salts which are physiologically acceptable include acid addition salts, particularly mineral acid salts, such as hydrochloride and sulfuric acid salt.

Examples of the thiocyanic acid salts are physiologically acceptable one and include alkali metal salts, such as sodium or potassium salt, and alkaline earth metal salts, such as magnesium or calcium salt.

Examples of the alkali metal iodides include, for example, sodium or potassium iodide which is physiologically acceptable.

The stabilizer used in this invention exerts its stabilizing effect when incorporated in a proportion of at least 1.5% (w/v) and preferably about 1.5 to about 20% (w/v) relative to the precursor solution of a titer of 100 to 2,000 IU/ml. The symbol "% (w/v)" herein and in Claim means 1 g of a solute in 100 ml of a solution containing the solute.

In this invention, the above-mentioned stabilizer is added at any period wherein the precursor is subjected to conditions which possibly inactive the precursor, for example when the precursor is made into medical preparations or when the precursor preparation is being stored.

It is needless to say that other stabilizers may also be added in this invention. For instance, inorganic salts (for example, sodium chloride and sodium citrate) and organic salts (for example, those of ascorbic acid and glutamic acid) are favorably added.

The stabilizers used in this invention exert a strong stabilizing action for the precursor. Consequently, according to the method of this invention, the precursor does not lose its activity even in solutions and remains stable even when subjected to lyophilization and thawing.

EXAMPLE 1

An amount of the precursor obtained by the method described in Japanese Patent Application No. 170354/83, which corresponds to 210 IU/ml was mixed with various concentrations of KSCN, and each of the resulting mixtures was divided into two portions. One portion was maintained at 5° for 30 minutes and then examined for its titer.

The other portion was subjected 5 times to repeated freezing and thawing of 3 minutes each in a dry ice-ethanol mixture (about −30° C.) and in a thermostat kept at 37° C., respectively, and then examined for its titer.

The results of respective titer determinations are as shown in Table 1. The titers shown in Table 1 are expressed in percentage of remaining activity relative to the titer before the above-mentioned treatment.

The procedure of titer determination is as follows:

To 0.1 ml of a specimen, was added 0.1 ml of a plasmin solution, and the mixture was incubated at 37° C. for 10 minutes. The resulting mixture was further mixed with 1 ml glutamyl-glycyl-arginyl-p-methyl coumarrylamide and was incubated at 37° C. for 20 minutes. The resulting solution was mixed with 1.5 ml of 18% acetic acid and the mixture was examined for its fluorescence intensity at a excitation wave length of 370 nm and a fluorescence wave length of 460 nm. Reagents for titer determination (p-MCA method)

(1) Gelatin buffer solution

Into distilled water were dissolved 6.09 g of tris (hydroxymethyl) aminomethane, 5.84 g of NaCl and 10.0 g of gelatin (mfd. by Difco Co.). The solution was adjusted to pH 8.60 with 2N-HCl, the made up to 1 liter, and sterilized in an autoclave at 121° C. for 20 minutes.

(2) p-MCA solution

To one vial of glutamyl-glycyl-arginyl-p-methyl coumarrylamide manufactured by Protein Research Promotion Association, a foundation, was added 1 ml of dimethyl sulfoxide (DMSO) to form a solution. The solution was diluted with the buffer solution (1) and filled up to 100 ml. The resulting MCA concentration was 0.1 mM. This solution was prepared just before use.

(3) Plasmin solution

One vial (25 CU) of "plasmin for Labochem" (mfd. by Green Cross Co., Ltd.) was dissolved in 5 ml of the buffer solution (1). The resulting solution was divided into 0.1 ml portions and frozen for storage. The frozen product was diluted by adding 2.4 ml of the buffer solution (1) to a concentration of; 0.2 CU/ml before use.

(4) 18% Acetic acid

Acetic acid, 18 ml, was diluted with distilled water and made up to 100 ml.

TABLE 1

| Concentration of KSCN | Retention of activity (%) | |
|---|---|---|
| (% (w/v)) | Storage at 5° C. | Freeze-thawing |
| 0 | 90 | 64 |
| 1.0 | 99 | 67 |
| 2.5 | 99 | 88 |
| 5 | 100 | 87 |
| 10 | 100 | 90 |
| 20 | 100 | 89 |

Example 2

An amount of the precursor obtained by the method described in Japanese Patent Application No. 170354/83 corresponding to 740 IU/ml was mixed with various kinds of additives and the resulting mixtures were examined for their stabilizing effect in the same manner as in Example 1. The results obtained are as shown in Table 2.

TABLE 2

| Additive | Additive concentration (% w/v) | Retention of activity[2] (%) Storage at 5° C. | Retention of activity[2] (%) Freeze-thawing |
|---|---|---|---|
| None | — | 64 | 22 |
| Albumin | 4.0 | 98 | 72 |
| gelatin | 1.8 | 97 | 67 |
| Polyethylene glycol (M.W. 4000) | 10 | 82 | 50 |
| Pluronic ® F68[1] | 2.0 | 98 | 91 |
| Sodium mandelate | 5.0 | 91 | 76 |
| Triethanolamine | 1.5 | 92 | 55 |
| Ac—Gly—Lys—OMe acetate | 2.0 | 71 | 57 |
| Guanidine hydrochloride | 9.5 | 88 | 61 |
| Potassium thiocyanate | 5.0 | 93 | 67 |
| Potassium iodide | 16.6 | 95 | 58 |
| Serine | 2.0 | 70 | 45 |

Note:
[1]Pluronic ® F68 is a polyoxyethylene-polyoxypropylene copolymer.
[2]Retention of activity represents a value calculated based on the activity before treatment taken as 100%.

What is claimed is:

1. A stabilized urokinase precursor composition which comprises a urokinase precursor and at least one stabilizer thereof selected from the group consisting of polyoxyethylene-polyoxypropylene copolymers having a molecular weight of 2,000 to 20,000, mandelic acid salts, acid addition salts of acetylglycillysine methyl ester, guanidine salts, thiocyanic acid salts and alkali metal iodides in an amount sufficient for stabilizing the precursor, the salt being physiologically acceptable.

2. The composition of claim 1, wherein the urokinase precursor is obtained according to a method comprising culturing the precursor-producing cells derived from human kidney in a serum-free tissue culturing medium to produce the precursor, subjecting the supernatant of the culture fluid to purification with respect to protein therein, and subjecting the resulting protein solution containing the precursor to affinity chromatography using a column of immobilized anti-precursor antibody.

3. The composition of claim 1, which is an aqueous solution of the urakinase precursor and the stabilizer.

4. The composition of claim 3, wherein the amount sufficient for stabilizing the precursor is at least about 1.5% (w/v) relative to the aqueous solution containing the precursor in a concentration of 100 to 2,000 IU/ml.

5. The composition of claim 4, wherein the amount is about 1.5% to about 20% (w/v).

6. A method of stabilizing a urokinase precursor characterized by adding to a solution of the precursor at least one stabilizer thereof selected form the group consisting of polyoxyethylene-polyoxypropylene copolymers having a molecular weight of 2,000 to 20,000, mandelic acid salts, acid addition salts of acetylglycillsine methyl ester, guanidine salts, tiocyanic acid salts and alkali metal iodides in an amount sufficient for stabilizing the precursor, the salts being physiologically acceptable.

7. The method of claim 6, wherein the urokinase precursor is obtained according to a method comprising culturing the precursor-producing cells derived from human kidney in a serum-free tissue culturing medium to produce the precursor, subjecting the supernatant of the culture fluid to purification with respect to protein therein and subjecting the resulting protein solution containing the precursor to affinity chromatography using a column of immobilized anti-precursor antibody.

8. The method of claim 6, wherein the amount sufficient for stabilizing the precursor is at least about 1.5% (w/v) relative to the aqueous solution containing the precursor in a concentration of 100 to 2,000 IU/ml.

9. The method of claim 8, wherein the amount is about 1.5% to about 20% (w/v).

10. The composition of claim 1, wherein the urokinase precursor has a single-chained structure consisting of 411 amino acids, has a molecular weight of 53,000, has no enzymatic activity, and its plasminogen activator activity is manifested by plasmin treatment, the plasminogen activator activity being completely inhibited by antiurokinase antibody.

* * * * *